United States Patent [19]
Sikorski et al.
[11] 4,428,765
[45] Jan. 31, 1984

[54] THIOSULFENAMIDE DERIVATIVES OF N-PHOSPHONOMETHYLGLYCINE TRIESTERS AS HERBICIDES

[75] Inventors: James A. Sikorski, Lafayette, Ind.; Tommie G. Curtis, University City, Mo.

[73] Assignee: Monsanto Company, St. Louis, Mo.

[21] Appl. No.: 309,322

[22] Filed: Oct. 5, 1981

[51] Int. Cl.$^{3}$ ........................ A01N 57/30; C07F 9/40
[52] U.S. Cl. ........................................ 71/87; 260/941
[58] Field of Search ............................ 260/941; 71/87

[56] References Cited

U.S. PATENT DOCUMENTS

| | | | |
|---|---|---|---|
| 2,807,615 | 9/1957 | Himel | 568/102 |
| 3,932,403 | 1/1976 | Ashton et al. | 260/941 |
| 4,120,689 | 10/1978 | Dutra | 71/86 |
| 4,252,554 | 2/1981 | Dutra et al. | 71/87 |
| 4,329,293 | 5/1982 | Ager et al. | 260/968 |

*Primary Examiner*—Anton H. Sutto
*Attorney, Agent, or Firm*—Gordon F. Sieckmann; Raymond C. Loyer; Howard C. Stanley

[57] ABSTRACT

This invention relates to thiosulfenamide derivatives of N-phosphonomethylglycine which are useful as herbicides. This invention further relates to herbicidal compositions containing such derivatives and to herbicidal methods employing such compounds and compositions, and a process for preparing such compounds.

33 Claims, No Drawings

THIOSULFENAMIDE DERIVATIVES OF N-PHOSPHONOMETHYLGLYCINE TRIESTERS AS HERBICIDES

This invention relates to thiosulfenamide derivatives of N-phosphonomethylglycine which are useful as herbicides. This invention further relates to herbicidal compositions containing such derivatives and to herbicidal methods employing such compounds and compositions, and a process for preparing such compounds.

U.S. Pat. No. 4,120,689 issued to Gerard A. Dutra on Oct. 17, 1978 discloses alkyl-[di(benzyl) or di(aryl)] esters of N-phosphonomethyl glycine prepared by the reaction of a dibenzyl or diaryl phosphite with an N-methylene lower alkyl glycinate trimer. These esters and the hydrolysis products thereof containing at least one benzyloxy or aryloxy group bonded to the phosphorus atom thereof are disclosed as compounds having the formula

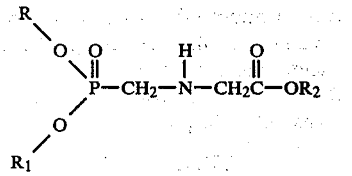

wherein R of U.S. Pat. No. 4,120,689, supra is disclosed as a member of the group consisting of phenyl, benzyl, naphthyl, biphenylyl, benzyloxyphenyl and phenyl, benzyl or naphthyl groups substituted with from 1 to 3 groups selected from the class consisting of hydroxyl, lower alkyl, lower alkoxy, lower alkylthio, trifluoromethyl, carbo (lower alkoxy), nitro, or halo; $R_1$ of U.S. Pat. No. 4,120,689, supra is hydrogen or an R group, and $R_2$ of U.S. Pat. No. 4,120,689, supra is a lower alkyl group or hydrogen and the strong acid salts of the compounds wherein neither $R_1$ or $R_2$ is H. A post-emergent herbicide utility is disclosed.

The compounds of the present invention are represented by the formula

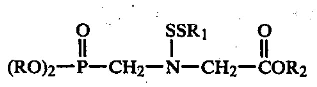

(I)

wherein R is selected from the group consisting of phenyl, naphthyl, biphenylyl; or phenyl, naphthyl or biphenylyl substituted with from 1 to 3 substituents independently selected from the group consisting of lower alkyl, lower alkoxy, lower alkylthio, lower alkoxycarbonyl, methylenedioxy, trifluoromethyl, cyano, nitro and halogen; $R_1$ is independently alkyl, cycloalkyl, aralower alkyl, phenyl, naphthyl, or phenyl substituted with from 1 to 3 substituents selected from the group consisting of lower alkyl, lower alkoxy, halogen, trifluoromethyl and $R_2$ is independently lower alkyl or aralower alkyl.

It is preferred that R is phenyl or phenyl substituted with lower alkoxy. Also, it is preferred that the substituted phenyl groups represented by R contain 1 or 2 substituents. It is preferred herein that $R_1$ is independently alkyl or tertiary alkyl, and that $R_2$ is lower alkyl.

Illustrative of the substituted phenyl groups which R and $R_1$ independently represent are mono-substituted phenyl wherein the substituent is in the ortho, meta or para position, for example, methylphenyl, butylphenyl, methoxyphenyl, butoxyphenyl, fluorophenyl, chlorophenyl, bromophenyl, iodophenyl, trifluoromethylphenyl, nitrophenyl, methylthiophenyl, butylthiophenyl, cyanophenyl, ethoxycarbonylphenyl, and the like, and the di- and tri- substituted phenyl groups wherein the substituents are the same or different and are located in the 2, 3, 4, 5 or 6 positions of the phenyl ring, for example, dichlorophenyl, dimethylphenyl, methylchlorophenyl, ethylfluorophenyl, dibutoxyphenyl, butylnitrophenyl, methylthiochlorophenyl, di(ethylthio)phenyl, trimethylphenyl, trichlorophenyl, tributylphenyl, ethyldichlorophenyl and the like.

Groups representative of a substituted naphthyl groups represented by R include methylnaphthyl, nitronaphthyl, bromonaphthyl, dimethylnaphthyl, difluoronaphthyl, trimethylnaphthyl and the like.

Groups representative of substituted biphenylyl groups represented by R include methylbiphenylyl, nitrobiphenylyl, bromobiphenylyl, dimethylbiphenylyl, difluorobiphenylyl, trimethylbiphenylyl and the like.

As employed herein, the term "lower alkyl" designates alkyl radicals which have from 1 to 4 carbon atoms in a straight or branched chain, such as, for example, methyl, ethyl, propyl, isopropyl, butyl, isobutyl, sec-butyl, and t-butyl.

As employed herein, the term "tertiary alkyl" includes alkyl and substituted alkyl radicals having 4 to 10 carbon atoms therein, preferably having 4 to 8 carbon atoms therein. Typically tertiary alkyl groups include tertiary butyl, tertiary hexyl and tertiaryr amyl.

As employed herein, the term "aralower alkyl" includes combinations of those groups as aforedefined for the term "lower alkyl" with aryl groups such as phenyl, benzyl, naphthyl and biphenylyl.

Typical groups representative of aralower alkyl include phenylmethyl, phenylethyl, phenylpropyl, phenylbutyl and the like.

The term "halo" or "halogen" as employed herein means chlorine, bromine, iodine and fluorine.

The term "lower alkoxy" includes groups representative of the term "lower alkyl" in combination with oxygen and includes methoxy, ethoxy, propoxy, butoxy mixtures thereof and the like.

The term "lower alkylthio" includes representatives of lower alkyl in combination with sulfur.

The term "lower alkoxycarbonyl" includes groups representative of the aforedefined term "lower alkoxy" in combination with a carbonyl group.

In accordance with the present invention, thiosulfenamide derivatives of N-phosphonomethylglycine of formula (I) are prepared by reacting a compound of the formula

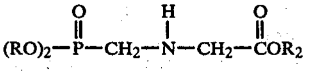

(II)

wherein R and $R_2$ are as above defined; in an aprotic solvent, with a thiosulfenyl chloride of the formula $$R_1—SS—Cl \qquad (III)$$

wherein $R_1$ is as above defined; in the presence of a hydrogen chloride acceptor.

The reaction temperature is in the range from about 0° to about 100° C. However, for ease of reaction and recovery of product, it is preferred to conduct the process of the present invention within a range of about 0° to about 30° C. although greater or lower temperatures can be employed if desired.

In preparing the novel compounds of formula (I), the ratio of reactants of formulas (II) and (III), is not narrowly critical. For best results, however, for each mole of a compound of formula (II), one should employ one mole of a thiosulfenyl chloride of formula (III) to produce one mole of a compound of formula (I). It is preferred to employ an excess of a thiosulfenyl chloride of formula (III) for ease of reaction and maximum yield of product of formula (I). The hydrogen chloride acceptor is preferably used in stoichiometric excess to insure completeness of reaction.

The hydrogen chloride acceptor is typically an amine, preferably a tertiary amine, which will not react with the reactants employed or products formed. Examples of suitable tertiary amine hydrogen chloride acceptors include trimethylamine, triethylamine, tributylamine, trihexylamine, 1,5-diazabicyclo-[5.4.0]-undec-5-ene, pyridine, quinoline, mixtures thereof and the like.

Due to the reactive nature of the various reaction intermediates and reactants, the process of the present invention should be conducted in an aprotic solvent under essentially anhydrous conditions. Illustrative of the aprotic solvents employed in the process of this invention include benzene, toluene, tetrahydrofuran, cyclohexane, methylcyclohexane, hexane, octane, dioxane, ethyl ether, dichloromethane and the like.

While the processes of this invention can be conducted at atmospheric, sub-atmospheric or superatmospheric pressure, for convenience and economy it is generally preferred to conduct these processes at atmospheric pressure.

Methods which may be employed for preparing compounds of formula (I) wherein $R_1$ is alkyl and cycloalkyl include those processes wherein an amine is reacted with an alkylthiosulfenyl halide. Included also are those processes wherein a halogen, an amine, and a disulfide and/or mercaptan are interacted in a single reaction step to form a thiosulfenamide. Another acceptable process includes a multistep process wherein a disulfide and/or mercaptan is reacted with a halogen to produce an organic sulfur containing halide and wherein a resulting mixture is then admixed with an amine under conditions causing reaction of halide therein with amine to produce a thiosulfenamide. The aforementioned processes are particularly described in U.S. Pat. No. 2,807,615 issued to Chester M. Himel on Sept. 24, 1957 which is incorporated herein by reference in its entirety.

Methods which may be employed for preparing compounds of formula (I) wherein $R_1$ is phenyl, naphthyl, aralower alkyl or phenyl or naphthyl substitued as aforedefined include a method for the preparation of arylthiosulfenyl chlroide comprising reacting a thiophenol and sulfur dichloride such as is described in Bull Chem. Soc. Japan 43, 3615 (1970), Tamotsu Fujisawa, and Gen-ichi Tsuchihashi, which is incorporated herein in its entirety by reference.

The following illustrative, non-limiting examples will serve to further demonstrate to those skilled in the art the manner in which specific compounds within the scope of this invention can be prepared. In the examples, all parts are parts by weight unless otherwise expressly stated.

GENERAL PROCEDURE FOR PREPARING THE COMPOUNDS OF EXAMPLES I AND II

A pentane solution of tert-butylthiosulfenyl chloride was prepared as follows: Chlorine gas (3.5 ml, 0.3 mol) was condensed under nitrogen at −78° C. and then passed via double-ended needle into a solution of di-tertbutyl-disulfide (17.8 g, 0.1 mol) in 150 ml of pentane at −20° C. at such a rate that the temperature did not exceed −15° C. The resulting orange solution was then stirred at −15° C.±5° C. for 3 hours, cooled to −20° C. and added via cannula to a cold solution of the appropriate compound of formula (II) (0.03 mol) and triethylamine (10.1 g, 0.1 mol) in 150 ml of toluene at such a rate that the temperature did not exceed +5° C. The resulting yellow reaction mixture was allowed to come to room temperature over 2-3 hours. The precipitate of triethylamine hydrochloride was removed by filtration. The toluene filtrate was washed twice with 100 ml of cold 10% aqueous NaOH, twice with cold water, dried over $MgSO_4$, filtered and concentrated on a rotovap to give the crude product which was purified on a 1"×4' column of oven-dried silica gel using 70% cyclohexane 30% ethyl acetate as the eluent.

$^1$H NMR, $^{31}$P NMR, FDMS and elemental analysis were all consistent with pure products.

EXAMPLE I

Glycine, N[(1,1-dimethylethyl)dithio]-N-[(diphenoxyphosphinyl)methyl]-, methyl ester, hemihydrate corresponding to a compound of formula (I) wherein R is phenyl and $R_1$ is 1,1-dimethylethyl and $R_2$ is methyl was prepared by the aforerecited procedure as a yellow oil having an analysis for $C_{20}H_{26}NO_5PS_2.\frac{1}{2}H_2O$ Calculated: C,51.71; H,5.86; N,3.02; S,13.80; Found: C,51.90; H,5.89; N,2.86; S,13.31.

EXAMPLE II

Glycine, N-[[bis(4-methoxyphenoxy)phosphinyl]methyl]-N-[(1,1-dimethylethyl)dithio]-, ethyl ester corresponding to a compound of formula (I) wherein R is 4-methoxy phenyl and $R_1$ is 1,1-dimethylethyl and $R_2$ is ethyl was prepared by the aforerecited procedure as a yellow oil $n_D^{25}=1.5503$ having an analysis for $C_{23}H_{32}NO_7PS_2$:

Calculated: C,52.16; H,6.09; N,2.64; S,12.11; Found: C,52.27; H,6.10; N,2.64; S,12.23.

EXAMPLE III

Tert-butylthiosulfenyl chloride was generated in situ using the aforerecited literature methods of U.S. Pat. No. 2,807,615 supra. This solution was then transferred via double-ended needed under nitrogen into a cold toluene solution of glycine, N-[[(Diphenoxy)phosphinyl]methyl]-, phenylmethyl ester, (12.0 g, 0.029 mol) and triethylamine. The mixture was then allowed to warm to room temperature slowly. The reaction was stirred over night. The mixture was then filtered to remove the triethylamine hydrochloride. The toluene filtrate was washed with equal volumes of cold 10% aqueous NaOH and cold water, dried over $MgSO_4$, and then the material was adsorbed onto silica gel. Purification by HPLC on a 1"×4' silica gel column gave the desired pure product. $^1$H NMR, $^{31}$P NMR, FDMS and elemental analyses were all consistent with pure product: glycine, N-[(1,1-dimethylethyl)dithio]-N-[(diphenoxyphosphinyl)methyl]-, phenyl-methyl ester, corresponding to a compound of formula (II) wherein R is phenyl and $R_1$ is 1,1dimethylethyl and $R_2$ is phenylmethyl was prepared as a yellow oil having a refractive index $n_D^{25}=1.5674$ and an analysis for $C_{26}H_{30}NO_5PS_2$:

Calculated: C,58.74; H,5.69; N,2.63; S,12.06; Found: 58.49; H,5.77; N,2.57; S,12.23.

EXAMPLE IV

A pentane solution of p-toluenethiosulfenyl chloride (0.03 mol) was prepared from p-thiocresol (3.7 g, 0.03 mol) and sulfur dichloride (3.1 g, 0.03 mol), and then added to a solution of the glyphosate triester glycine, N-[(diphenoxyphosphinyl)methyl]-, methyl ester (8.0 g, 0.025 mol) and triethylamine (2.5 g, 0.025 mol) in 200 ml of toluene at 0° C. The reaction mixture was then allowed to gradually warm to room temperature over a 2.5 hour period. The precipitate of triethylamine hydrochloride was removed by filtration. The yellow toluene filtrate was washed with cold 10% aqueous NaOH and cold water, dried over $MgSO_4$, filtered, and then adsorbed onto silica gel. Purification by HPLC on a 1"×4' silica gel column gave the desired product glycine, N-[diphenoxyphosphinyl)methyl]-N-[(4-methylphenyl)dithio]-, methyl ester corresponding to a compound of formula (I) wherein R is phenyl, $R_1$ is 4-methylphenyl and $R_2$ is methyl as a yellow solid, 4.5 g (37%), having a melting point of 69°-72° C., NMR (−14.54 ppm) and an analysis for $C_{23}H_{24}N_1O_5P_1S_2$ was:

Calculated: C,56.43; H,4.94; N,2.86; S,13.10; Found: C,56.59; H,4.99; N,2.87; S,13.07.

GENERAL PROCEDURE FOR PREPARING THE COMPOUNDS OF FOR EXAMPLES V AND VI

A solution of the thiosulfenyl chloride was prepared by adding a toluene solution of the appropriate mercaptan to a solution of sulfur dichloride in toluene at −20° C. under a nitrogen atmosphere. The reaction mixture was stirred at −20° C. for 3 hours and then was added via cannula to a solution of the glyphosate triester and triethylamine in toluene at 0° C. The reaction mixture was stirred for 3 hours, allowing to warm to room temperature during the final ½ hour. The triethylamine hydrochloride was removed by filtration and the filtrate was washed with cold 10% aqueous NaOH followed by cold water, dried over $MgSO_4$, filtered and adsorbed onto silica gel. Purification by HPLC on a 1"×4' column of silica gel, eluting with 30-40% ethylacetate/cyclohexane gave the desired thiosulfenamide. $^1H$ NMR, $^{31}P$ NMR and elemental analyses were all consistent with pure product.

EXAMPLE V

Glycine, N-[[bis(4-methoxyphenoxy)phosphinyl]methyl]-N-[(2-naphthalenyl)dithio]-, phenylmethyl ester corresponding to a compound of formula (I) wherein R is 4-methoxyphenyl, $R_1$ is 2-naphthyl and $R_2$ is phenylmethyl was prepared following the aforerecited general procedure as a yellow oil having a refractive index $n_D^{25}=1.6110$ and an analysis for $C_{34}H_{32}NO_7PS_2$:

Calculated: C,61.72; H,4.87; N,2.12; S,9.69; Found: C,61.58; H,4.95; N,2.08; S,9.60.

EXAMPLE VI

Glycine, N-[[bis(4-methoxyphenoxy)phosphinyl]methyl]-N-[(4-chlorophenyl)dithio]-, phenylmethyl ester corresponding to a compound of formula (I) wherein R is 4-methoxyphenyl, $R_1$ is 4-chlorophenyl and $R_2$ is phenylmethyl was prepared as an orange oil having a refractive index $n_D^{25}=1.5980$ and an analysis for $C_{30}H_{29}ClNO_7PS_2$:

Calculated: C,55.77; H,4.52; N,2.17; S,9.93; Found: C,55.91; H,4.58; N,2.12; S,9.84.

Other compounds of this invention which have been prepared also include those hereafter enumerated. While these compounds have been prepared by a different process disclosed and claimed in patent application AG-2059 "Process For Preparing Thiosulfenamide Derivatives Of N-Phosphonomethylglycine Triesters" filed simultaneously herewith, preparation of these compounds is believed also consistent with the process of this invention.

GENERAL PROCEDURE FOR THE PREPARATION OF THIOSULFENAMIDES

For Examples VII, VIII, IX, X and XI hereafter following

An oven-dried 1 liter flask was cooled under nitrogen, and charged with sulfur dichloride (0.05 mol) and 300 ml of toluene and cooled to −20° C. To it was added a toluene solution of formula (II) (0.05 mol) corresponding to the particular thiosulfenamide desired at such a rate that the temperature did not exceed −5° C. The yellow reaction mixture was stirred at −20° C. for 3½ hours. The supernatant liquid was removed under nitrogen and concentrated in vacuo to yield the desired intermediate glyphosate sulfenyl chloride as an oil. A toluene solution of the oil was added slowly to a solution of the appropriate mercaptan in triethylamine in toluene at 5° C., maintaining the temperature below 10° C. The yellow reaction mixture was stirred for 3-4 hours, with slow warming to room temperature. The triethylamine hydrochloride was removed by filtration and the filtrate was washed with cold 10% aqueous sodium hydroxide, cold water, dried over $MgSO_4$, and concentrated in vacuo to an oil. Purification by HPLC gave the desired thio-sulfenamide product of the formula (I) as a yellow oil. $^1H$ NMR, $^{31}P$ NMR, and elemental analyses were all consistent with pure products.

EXAMPLE VII

Glycine, N-[(diphenoxyphosphinyl)methyl]-N-[(1-methylethyl)-dithio]-, methyl ester corresponding to a compound of formula (I) wherein R is phenyl, $R_1$ is isopropyl and $R_2$ is methyl was prepared as a yellow oil having a refractive index of 1.5567 at 22.3° C. and an analysis for $C_{19}H_{24}NO_5PS_2$:

Calculated: C,51.69; H,5.48; N,3.17; S,14.52; Found: C,51.67; H,5.50; N,3.15; S,14.57.

EXAMPLE VIII

Glycine, N-[(diphenoxyphosphinyl)methyl]-N-(octyldithio)-, methyl ester corresponding to a compound of formula (I) wherein R is phenyl, $R_1$ is n-octyl, and $R_2$ is methyl was prepared as a yellow oil having a refractive index of 1.5415 at 23.3° C. and an analysis for $C_{24}H_{34}NO_5PS_2$:

Calculated: C,56.34; H,6.70; N,2.74; S,12.53; Found: C,56.37; H,6.64; N,2.63; S,12.05.

EXAMPLE IX

Glycine, N-(cyclohexyldithio)-N- [(diphenoxyphosphinyl)methyl]-, phenylmethyl ester corresponding to a compound of formula (I) wherein R is phenyl, $R_1$ is cyclohexyl, and $R_2$ is phenylmethyl was prepared as a yellow oil having a refractive index of 1.5752 at 25° C. and an analysis for $C_{28}H_{32}NO_5PS_2$:

Calculated: C,60.31; H,5.78; N,2.51; S,11.50; Found: C,59.96; H,5.73; N,2.34; S,10.67.

EXAMPLE X

Glycine, N-[(diphenoxyphosphinyl)methyl]-N-[(2-phenylethyl)dithio]-, phenylmethyl ester corresponding to a compound of formula (I) wherein R is phenyl, $R_1$ is phenylethyl, and $R_2$ is phenylmethyl was prepared as a yellow oil having a refractive index of 1.5956 at 23° C. and an analysis for $C_{30}H_{30}NO_5PS_2$:

Calculated: C,62.16; H,5.22; N,2.42; S,11.06; Found: C,60.90; H,5.29; N,2.23; S,10.08.

EXAMPLE XI

Glycine, N-[[Bis(2-methoxyphenoxy)phosphinyl]-merthyl]-N-[(3-(trifluoromethyl)phenyl)dithio]-, methyl ester corresponding to a compound of formula (I) wherein R is 2-methoxyphenyl, $R_1$ is 3-trifluoromethylphenyl, and $R_2$ is methyl was prepared as a yellow oil having a refractive index of 1.5685 at 21.8° C. and an analysis for $C_{25}H_{25}F_3NO_2PS_2$:

Calculated: C,49.75; H,4.17; N,2.32; S,10.62; Found: C,49.60; H,4.22; N,2.27; S,10.70.

EXAMPLE XII

Glycine, N-[[bis(4-methoxyphenoxy)phosphinyl]methyl]-N-(methyldithio)-, ethyl ester. An oven-dried 500 ml flask, cooled under nitrogen, was charged with 200 ml of toluene and cooled to −20° C. and the sulfur dichloride (8.7 g, 0.085 mol) was added. To this solution was added slowly via cannula a toluene solution of glycine, N-[di(4-methoxyphenoxy)phosphinyl)methyl],-ethyl ester (34.8 g, 0.085 mol) at such a rate to maintain the temperature below −10° C. The green reaction mixture was stirred for 3½ hours at −20° C. The supernatant liquid was removed under nitrogen and concentrated in vacuo to 22 g (54% crude) of a dark oil. A toluene solution of the oil was added slowly via cannula to a solution of excess methyl mercaptan and two equivalents of triethylamine in toluene at 0° C. The rate of addition was such that the temperature did not exceed 10° C. The reaction mixture was stirred under nitrogen for 2 hours, allowing to slowly warm to room temperature. The triethylamine hydrochloride was removed by filtration and the filtrate was washed with cold 10% aqueous sodium hydroxide, cold water, dried over $MgSO_4$, filtered, and concentrated to an oil. Purification on a Waters Prep Pak 500 silica gel column, eluting with 40% ethylacetate/ 60% cyclohexane gave the desired product as a yellow oil, 3.4 g (30%) corresponding to a compound of formula (I) wherein R is 4-methoxyphenyl, $R_1$ is methyl, and $R_2$ is ethyl, $n_D^{22.4}$=1.5580 having an analysis for $C_{20}H_{26}N_1O_7P_1S_2$;

Calculated: C,49.27; H,5.38; N,2.87; S,13.15. Found: C,49.35; H,5.39; N,2.81; S,13.09.

EXAMPLE XIII

An oven-dried 500 ml flask was charged with 200 ml of toluene, cooled to −20° C., and charged with sulfur dichloride (2.0 g, 0.02 mol). To this solution was added slowly via cannula a toluene solution of glycine, N-[[bis(4-chloro-3-methylphenoxy)phosphinyl]methyl]-, ethyl ester (7.0 g, 0.016 mol) and triethylamine, maintaining the temperature below −10° C. The reaction mixture was stirred at −20° C. for 2½ hours. The supernatant liquid was removed under nitrogen and slowly added via cannula to a solution of 4-methoxybenzenethiol (2.2 g, 0.016 mol) and triethylamine in toluene at −10° C. The reaction mixture was stirred overnight. The triethylamine hydrochloride was removed by filtration and the brown filtrate was washed with cold 10% aqueous sodiumhydroxide and cold water, dried over magnesium sulfate, filtered and concentrated in vacuo to 7.2 g of brown oil. Purification by HPLC on a Waters Prep Pak 500 silica gel column, eluting with 10% ethylacetate, 90% cyyclohexane yielded 1.3 g of yellow oil corresponding to a compound of formula (I) wherein R is 4-chloro-3-methylphenyl, $R_1$ is 4-methoxyphenyl and $R_2$ is ethyl. The product had a refractive index of 1.5738 at 24° C. and an elemental analysis for $C_{26}H_{28}Cl_2N_1O_6PS_2$:

Calculated: C,50.65; H,4.58; N,2.27; S,10.40 Found: C,50.39; H,4.61; N,2.23; S,10.52.

EXAMPLE XIV

An oven-dried 500 ml flask cooled under nitrogen was charged with 150 ml of toluene, cooled to −20° C. and sulfur dichloride (6.2 g, 0.06 mol) was added. To this solution was added slowly via cannula a solution of glycine, N-[(diphenoxyphosphinyl)methyl]-, methyl ester (20.0 g, 0.06 mol) and excess triethylamine in 150 ml of toluene, at such a rate that the temperature did not exceed −10° C. The orange-yellow reaction mixture was stirred at −20° C. for 2½ hours. The supernatant liquid was removed under nitrogen and added slowly via cannula to a solution of tert-butyl mercaptan (5.4 g, 0.06 mol) and excess triethylamine in 100 ml of toluene at −20° C. The reaction mixture was allowed to slowly warm to room temperature and was stirred overnight. The triethylamine hydrochloride was removed by filtration and the filtrate was washed with cold 10% acqueous NaOH followed by cold water, dried over $MgSO_4$, filtered and concentrated in vacuo. Purification by HPLC on a Waters Prep Pak 500 silica gel column gave 11.5 g of clear oil, $n_D^{23.4}$=1.5535, corresponding to a compound of formula (I) glycine, N-[(1,1-dimethylethyl)dithio]-N-[(diphenoxyphosphinyl)methyl]-, methyl ester wherein R is phenyl, $R_2$ is methyl and $R_1$ is tert-butyl and having an analysis for $C_{20}H_{26}NO_5PS_2$:

Calculated: C,52.73; H,5.75; N,3.07; S,14.08; Found: C,52.68; H,5.76; N,3.06; S,14.03.

This product was the non-hydrated form corresponding to the product of Example I.

The term "cycloalkyl" includes cyclopropane, cyclobutane, cyclopentane, cyclohexane, cyclooctane and the like. Typical cycloalkyl include cyclic arrangements of carbon hydrogen atoms having 3 to 8 carbon atoms therein.

The term "alkyl" includes those alkyl radicals having 1 to 8 carbon atoms therein in a straight or branched chain, substituted or unsubstituted and includes groups representative of the term "lower alkyl".

EXAMPLE XV

The post-emergence herbicidal activity of some of the various compounds of this invention was demonstrated by greenhouse testing in the following manner. A good grade of top soil is placed in aluminum pans having holes in the bottom and compacted to a depth of 0.95 to 1.27 cm. from the top of the pan. A predetermined number of seeds of each of several dicotyledonous and monocotyledonous annual plant species and/or vegetative propagules for the perennial plant species are placed on the soil and pressed into the soil surface. The seeds and/or vegetative propagules are covered with soil and leveled. The pans are then placed on a sand bench in the greenhouse and watered from below as needed. After the plants reach the desired age (two to three weeks), each pan except for the control pans is removed individually to a spraying chamber and sprayed by means of an atomizer operating at a positive air pressure of approximately 1.46 kg/$cm^2$ absolute. The atomizer contains 6 ml. of a solution or suspension of the chemical. In that 6 ml., is an amount of a cyclohexanone emulsifying agent mixture to give a spray solution or suspension which contains about 0.4% by weight of the emulsifier. The spray solution or suspension contains a sufficient amount of the candidate chemical in order to give application rates corresponding to those set forth in the tables. The spray solution is prepared by taking an aliquot of a 1.0% by weight stock solution or suspension of the candidate chemical in an organic solvent such as acetone or tetrahydrofuran or in water. The emulsifying agent employed is a mixture comprising 35 weight percent butylamine dodecylbenzene sulfonate and 65 weight percent of a tall oil ethylene oxide condensate having about 11 moles of ethylene oxide per mole of tall oil. The pans are returned to the greenhouse and watered as before and the injury to the plants as compared to the control is observed at approximately two and four weeks as indicated in the tables under WAT and the results recorded. In some instances, the two-week observations are omitted.

The post-emergence herbicidal activity index used in Table I is as follows:

| Plant Response | Index |
|---|---|
| 0–24% control | 0 |
| 25–49% control | 1 |
| 50–74% control | 2 |
| 75–99% control | 3 |
| 100% control | 4 |

The plant species utilized in these tests are identified by letter in accordance with the following legend:

| | |
|---|---|
| A - Canada Thistle* | K - Barnyardgrass |
| B - Cocklebur | L - Soybean |
| C - Velvetleaf | M - Sugar Beet |
| D - Morningglory | N - Wheat |
| E - Lambsquarters | O - Rice |
| F - Smartweed | P - Sorghum |
| G - Yellow Nutsedge* | Q - Wild Buckwheat |
| H - Quackgrass* | R - Hemp Sesbania |
| I - Johnsongrass* | S - Panicum Spp |
| J - Downy Brome | T - Crabgrass |

*Established from vegetative propagules.

A dash (—) in the tables indicates that the particular species was absent in the test.

TABLE I

| Compound of Example No. | WAT | kg/h | A | B | C | D | E | F | G | H | I | J | K |
|---|---|---|---|---|---|---|---|---|---|---|---|---|---|
| I | 4 | 11.2 | — | 3 | 3 | 3 | 4 | 2 | 2 | 2 | 4 | 2 | 4 |
| | 4 | 5.6 | — | 3 | 3 | 2 | 3 | 1 | 1 | 4 | 4 | 2 | 3 |
| II | 4 | 11.2 | — | 2 | 2 | 2 | 2 | 2 | 2 | 4 | 3 | 1 | 3 |
| | 4 | 5.6 | — | 1 | 2 | 1 | 3 | 0 | 1 | 1 | 2 | 2 | 2 |
| III | 4 | 11.2 | — | 2 | 2 | 2 | 3 | 2 | 1 | 2 | 4 | 3 | 2 |
| | 2 | 5.6 | — | 1 | 1 | 2 | 1 | 0 | 1 | 0 | 0 | 0 | 2 |
| IV | 4 | 11.2 | 1 | 3 | 3 | 2 | 4 | 2 | 2 | 1 | 2 | 2 | 3 |
| | 4 | 5.6 | 1 | 2 | 2 | 2 | 3 | 2 | 2 | 1 | 3 | 1 | 3 |
| V | 2 | 11.2 | — | 1 | 0 | 0 | 0 | 0 | 0 | — | 0 | 0 | 0 |
| | 2 | 5.6 | — | 0 | 0 | 0 | 0 | 0 | 0 | 0 | 1 | 0 | 0 |
| VI | 4 | 56.0 | — | 1 | 0 | 0 | 0 | — | 0 | 0 | 0 | 0 | 0 |
| | 2 | 11.2 | — | 0 | 0 | 0 | 0 | 0 | 0 | 0 | 0 | 0 | 0 |
| | 2 | 5.6 | 0 | 0 | 0 | 0 | 0 | 0 | 0 | 0 | 0 | 0 | 0 |
| VII | 4 | 11.2 | 3 | 4 | 4 | 3 | 4 | 4 | 3 | 3 | 4 | 3 | 4 |
| | 4 | 5.6 | 2 | 4 | 3 | 4 | 3 | 4 | 3 | 4 | 3 | 3 | 4 |
| VIII | 4 | 11.2 | 1 | 3 | 3 | 2 | 4 | 4 | 2 | 1 | 3 | 1 | 2 |
| | 4 | 5.6 | 0 | 4 | 1 | 2 | 3 | 2 | 1 | 3 | 3 | 2 | 2 |
| IX | 4 | 11.2 | 0 | 2 | 1 | 2 | 2 | 1 | 0 | 2 | 1 | 1 | 2 |
| | 4 | 5.6 | 1 | 1 | 0 | 1 | 2 | 2 | 0 | 1 | 1 | 1 | 2 |
| X | 4 | 11.2 | 1 | 3 | 1 | 2 | 3 | 2 | 1 | 1 | 0 | 1 | 2 |
| | 4 | 5.6 | 0 | 1 | 0 | 2 | 3 | 1 | 0 | 2 | 2 | 0 | 2 |
| XI | 4 | 11.2 | 1 | 3 | 0 | 2 | 3 | 2 | 1 | 4 | 2 | 1 | 3 |
| | 4 | 5.6 | 0 | 2 | 1 | 1 | 3 | 1 | 1 | 1 | 1 | 1 | 3 |
| XII | 4 | 11.2 | 2 | 3 | 2 | 3 | 3 | 2 | 1 | 1 | 3 | 3 | 3 |
| | 4 | 5.6 | 1 | 2 | 1 | 2 | 3 | 2 | 1 | 0 | 2 | 2 | 4 |
| XIII | 4 | 11.2 | — | 2 | 1 | 1 | 2 | — | 1 | 1 | 2 | 2 | 3 |
| | 4 | 5.6 | — | 1 | 1 | 1 | 2 | — | 2 | 1 | 3 | 2 | 3 |

TABLE II

| Compound of Example No. | WAT | kg/h | L | M | N | 0 | P | B | Q | D | R | E | F | C | J | S | K | T |
|---|---|---|---|---|---|---|---|---|---|---|---|---|---|---|---|---|---|---|
| I | 4 | 5.6 | 4 | 4 | 3 | 3 | 3 | 3 | 4 | 2 | 4 | 4 | 4 | 4 | 3 | 3 | 3 | — |
| | 4 | 1.12 | 1 | 3 | 3 | 1 | 3 | 3 | 1 | 2 | 1 | 3 | 2 | 1 | 2 | 3 | 3 | — |
| | 4 | 0.28 | 0 | 0 | 1 | 0 | 1 | 1 | 1 | 1 | 0 | 1 | 0 | 0 | 1 | 1 | 2 | — |
| | 4 | 0.06 | 0 | 0 | 0 | 0 | 0 | 1 | 0 | 1 | 0 | 0 | 0 | 0 | 0 | 0 | 0 | 0 |

TABLE II-continued

| Compound of | | | Plant Species | | | | | | | | | | | | | | | |
|---|---|---|---|---|---|---|---|---|---|---|---|---|---|---|---|---|---|---|
| Example No. | WAT | kg/h | L | M | N | 0 | P | B | Q | D | R | E | F | C | J | S | K | T |
| II | 4 | 5.6 | 2 | 3 | 3 | 3 | 3 | 2 | 2 | 2 | 4 | 3 | 3 | 2 | 3 | 3 | 3 | — |
| | 4 | 1.12 | 1 | 2 | 1 | 1 | 2 | 1 | 1 | 2 | 1 | 2 | 1 | 1 | 2 | 3 | 2 | — |
| | 4 | 0.28 | 1 | 1 | 0 | 0 | 1 | 1 | 1 | 1 | 1 | 1 | 0 | 0 | 1 | 0 | 1 | — |
| III | 4 | 5.6 | 2 | 4 | 2 | 2 | 3 | 2 | 3 | 2 | 3 | 4 | 3 | 2 | 2 | 4 | 3 | — |
| | 4 | 1.12 | 1 | 1 | 1 | 0 | 2 | 2 | 2 | 2 | 1 | 2 | 2 | 1 | 1 | 3 | 3 | — |
| | 4 | 0.28 | 0 | 1 | 1 | 0 | 1 | 1 | 1 | 2 | 1 | 2 | 1 | 1 | 0 | 2 | 2 | — |
| IV | 4 | 5.6 | 2 | 2 | 3 | 2 | 3 | 3 | 3 | 2 | 4 | 4 | 4 | 3 | 2 | 3 | 3 | 4 |
| | 4 | 1.12 | 1 | 1 | 1 | 0 | 2 | 1 | 2 | 2 | 4 | 4 | 4 | 1 | 1 | 2 | 2 | 4 |
| | 4 | 0.28 | 1 | 1 | 0 | 0 | 1 | 1 | 0 | 1 | 0 | 3 | 4 | 0 | 0 | 1 | 2 | 2 |
| VII | 4 | 11.2 | 0 | 3 | 0 | 3 | 2 | 0 | 0 | 1 | 0 | 3 | 3 | 1 | 2 | 3 | 3 | 3 |
| | 4 | 5.6 | 3 | 4 | 3 | 3 | 3 | 3 | 3 | 3 | 4 | 4 | 4 | 4 | 2 | 3 | 4 | 4 |
| | 4 | 1.12 | 1 | 2 | 1 | 0 | 1 | 2 | 2 | 2 | 1 | 3 | 3 | 2 | 1 | 1 | 2 | 3 |
| | 2 | 0.28 | 0 | 0 | 0 | 0 | 0 | 0 | 0 | 0 | 0 | 0 | 0 | 1 | 0 | 1 | 1 | 0 |
| | 2 | 0.056 | 0 | 0 | 0 | 0 | 0 | 0 | 0 | 0 | 0 | 0 | 0 | 0 | 0 | 0 | 0 | 0 |
| VIII | 4 | 5.6 | 2 | 3 | 3 | 3 | 3 | 3 | 3 | 3 | 1 | 3 | 2 | 2 | 2 | 3 | 3 | 4 |
| | 4 | 1.12 | 0 | 0 | 0 | 1 | 1 | 1 | 0 | 1 | 0 | 2 | 1 | 0 | 0 | 0 | 1 | 2 |
| | 4 | 0.28 | 0 | 0 | 0 | 0 | 0 | 0 | 0 | 1 | 0 | 0 | 0 | 0 | 0 | 0 | 0 | 0 |
| X | 4 | 5.6 | 2 | 4 | 3 | 1 | 2 | 3 | 2 | 2 | 1 | 3 | 2 | 2 | 3 | 3 | 4 | 4 |
| | 4 | 1.12 | 0 | 3 | 1 | 0 | 0 | 1 | 0 | 0 | 0 | 3 | 1 | 0 | 0 | 0 | 0 | 2 |
| | 2 | 0.28 | 0 | 0 | 0 | 0 | 0 | 0 | 0 | 0 | 0 | 0 | 0 | 0 | 0 | 0 | 0 | 0 |
| XI | 4 | 5.6 | 1 | 2 | 3 | 1 | 0 | 3 | 0 | 1 | 1 | 3 | 2 | 1 | 0 | 1 | 3 | 3 |
| | 4 | 1.12 | 0 | 2 | 1 | 0 | 0 | 1 | 0 | 1 | 2 | 3 | 3 | 0 | 0 | 0 | 0 | 2 |
| | 2 | 0.28 | 0 | 0 | 0 | 0 | 0 | 0 | 0 | 0 | 0 | 0 | 0 | 0 | 0 | 0 | 0 | 0 |
| XII | 4 | 5.6 | 3 | 4 | 3 | 3 | 3 | 4 | 4 | 3 | 3 | 4 | 4 | 4 | 4 | 4 | 4 | 4 |
| | 4 | 1.12 | 1 | 1 | 1 | 0 | 2 | 3 | 1 | 2 | 0 | 2 | — | 1 | 2 | 2 | 3 | 4 |
| | 4 | 0.28 | 0 | 0 | 0 | 0 | 0 | 0 | 0 | 0 | 0 | 0 | 0 | 0 | 0 | 0 | 0 | 0 |

EXAMPLE XVI

The pre-emergent herbicidal activity of various compounds of this invention is demonstrated as follows. A good grade of top soil is placed in aluminum pans and compacted to a depth of 0.95 to 1.27 cm. from the top of each pan. A predetermined number of seeds or vegetative propagules of each of several plant species are placed on top of the soil in each pan and then pressed down. Herbicidal compositions prepared as in the previous example are applied by admixture with or incorporation in the top layer of soil.

In this method, the soil required to cover the seeds and propagules is weighed and admixed with a herbicidal composition containing a known amount of the active ingredient (compound of this invention). The pans are then filled with the admixture and leveled. Watering is carried out by permitting the soil in the pans to absorb moisture through apertures in the pan bottoms. The seed and propagule containing pans are placed on a wet sand bench and maintained for approximately two weeks under ordinary conditions of sunlight and watering. At the end of this period, the number of emerged plants of each species is noted and compared to an untreated control. The data is given in Table III.

The pre-emergent herbicidal activity index used below is based upon average percent control of each species as follows:

| Percent Control | Index |
|---|---|
| 0-24% control | 0 |
| 25-49% control | 1 |
| 50-74% control | 2 |
| 75-100% control | 3 |

Plant species in the table are identified by the same code letters used in the previous example.

TABLE III

| Compound of | | | Plant Species | | | | | | | | | | |
|---|---|---|---|---|---|---|---|---|---|---|---|---|---|
| Example No. | WAT | kg/h | A | B | C | D | E | F | G | H | I | J | K |
| I | 2 | 11.2 | — | 0 | 0 | 1 | 0 | 0 | 0 | 1 | 1 | 0 | 0 |
| II | 2 | 11.2 | — | 0 | 0 | 0 | 0 | 0 | 0 | 0 | 0 | 0 | 0 |
| III | 2 | 11.2 | — | 0 | 0 | 0 | 1 | 1 | 0 | 0 | 0 | 1 | 2 |
| IV | 2 | 11.2 | 2 | 0 | 1 | 1 | 1 | 0 | 1 | 1 | 1 | 0 | 0 |
| V | 2 | 11.2 | — | 0 | 0 | 1 | 0 | 0 | 0 | 0 | 0 | 0 | 0 |
| VI | 2 | 11.2 | — | 0 | 0 | 0 | 1 | 0 | 0 | 0 | 0 | 0 | 0 |
| VII | 2 | 11.2 | 3 | 1 | 0 | 1 | 3 | 2 | 3 | 3 | 0 | 2 | 2 |
| VIII | 2 | 11.2 | 1 | 0 | 0 | 0 | 0 | 0 | 0 | 0 | 2 | 0 | 0 |
| X | 2 | 11.2 | 1 | 0 | 0 | 0 | 0 | 0 | 0 | 0 | 0 | 0 | 0 |
| XI | 2 | 11.2 | 3 | 0 | 0 | 0 | 0 | 0 | 0 | 1 | 0 | 0 | 0 |
| XII | 2 | 11.2 | 2 | 0 | 0 | 1 | 0 | 1 | 0 | 1 | 3 | 2 | 3 |
| XIII | 2 | 11.2 | — | 0 | 0 | 0 | 0 | — | 0 | 0 | 0 | 0 | 0 |

From the test results presented in Tables I and II, it can be seen that the post-emergent herbicidal activity of the compounds of this invention is, for the most part, general in nature. In certain specific instances, however, some selectivity is demonstrated. In this regard it should be recognized that each individual species selected for the above tests is a representative member of a recognized family of plant species.

From Table III, it can be seen that the pre-emergent herbicidal activity demonstrated some selectivity.

The herbicidal compositions, including concentrates which require dilution prior to application to the plants, of this invention contain from 5 to 95 parts by weight of at least one compound of this invention and from 5 to 95 parts by weight of an adjuvant in liquid or solid form, for example, from about 0.25 to 25 parts by weight of wetting agent, from about 0.25 to 25 parts by weight of a dispersant and from 4.5 to about 94.5 parts by weight of inert liquid extender, e.g., water, acetone, tetrahydrofuran, all parts being by weight of the total composition. Preferably, the compositions of this invention contain from 5 to 75 parts by weight of at least one compound of this invention, together with the adjuvants. Where required, from about 0.1 to 2.0 parts by weight of the inert liquid extender can be replaced by a corrosion inhibitor such as ethanol mercaptan, sodium thiosulfate, dodecylmono or dimercaptan or anti-foaming agent such as a dimethylpolysiloxane, or both. The compositions are prepared by admixing the active ingredient with an adjuvant including diluents, extenders, carriers and conditioning agents to provide compositions in the form of finely-divided particulate solids, pellets, solutions, dispersions or emulsions. Thus, the active ingredient can be used with an adjuvant such as a finely-divided solid, a liquid of organic origin, water, a wetting agent, a dispersing agent, an emulsifying agent or any suitable combination of these.

The herbicidal compositions of this invention, particularly liquids and soluble powders, preferably contain as a conditioning agent one or more surface-active agents in amounts sufficient to render a given composition readily dispersible in water or in oil. The incorporation of a surface-active agent into the compositions greatly enhances their efficacy. By the term "surface-active agent", it is understood that wetting agents, dispersing agents, suspending agents and emulsifying agents are included therein. Anionic, cationic and nonionic agents can be used with equal facility.

Preferred wetting agents are alkyl benzene and alkyl naphthalene sulfonates, sulfated fatty alcohols, amines or acid amides, long chain acid esters of sodium isothionate, esters of sodium sulfosuccinate, sulfated or sulfonated fatty acid esters petroleum sulfonates, sulfonated vegetable oils, polyoxyethylene derivatives of phenols and alkylphenols (particularly isooctylphenol and nonylphenol) and polyoxyethylene derivatives of the mono-higher fatty acid esters of hexitol anhydrides (e.g., sorbitan). Preferred dispersants are methyl cellulose, polyvinyl alcohol, sodium lignin, sulfonates, polymeric alkyl naphthalene sulfonates, sodium naphthalene sulfonate, polymethylene bisnaphthalenesulfonate and sodium N-methyl-N-(long chain acid) taurates.

When operating in accordance with the present invention, effective amounts of the compounds or compositions of this invention are applied to the plants, or to soil containing the plants, or are incorporated into aquatic media in any convenient fashion. The application of liquid and particulate solid compositions to plants or soil can be carried out by conventional methods, e.g., power dusters, boom and hand sprayers and spray dusters. The compositions can also be applied from airplanes as a dust or a spray because of their effectiveness at low dosages. The application of herbicidal compositions to aquatic plants is usually carried out by adding the compositions to the aquatic media in the area where control of the aquatic plants is desired.

The application of an effective amount of the compounds or compositions of this invention to the plant is essential and critical for the practice of the present invention. The exact amount of active ingredient to be employed is dependent upon the response desired in the plant as well as such other factors as the plant species and stage of development thereof, and the amount of rainfall as well as the specific glycine employed. In foliar treatment for the control of vegetative growth, the active ingredients are applied in amounts from about 0.112 to about 56.0 or more kilograms per hectare. In pre-emergent treatments, the rate of application can be from about 5.6 to about 22.4 or more kilograms per hectare. In applications for the control of aquatic plants, the active ingredients are applied in amounts of from about 1.0 parts per million to about 1000 parts per million, based on the aquatic medium. An effective amount for phytotoxic or herbicidal control is that amount necessary for overall or selective control, i.e., a phytotoxic or herbicidal amount. It is believed that one skilled in the art can readily determine from the teachings of this specification, including examples, the approximate application rate.

There are several possible methods for applying liquid compositions of this invention to emerged plants. Such methods include the use of wiper systems whereby the plant to be treated is contacted with an absorbent material containing the particular liquid composition, a portion of which is thereby released onto the plant upon contact therewith. Such wiper systems typically comprise a reservoir of the liquid composition into which a portion of the absorbent material is placed and is fed therethrough. Generally, substances employable as absorbent material include substances of any shape or form capable of absorbing the liquid composition and releasing a portion of the same upon contact with the plant. Typical absorbent materials include felt, foam rubber, cellulose, nylon, sponges, hemp, cotton, burlap, polyester over acrylic, combinations thereof and the like. Forms of absorbent material include rope, twine, string, cloths, carpets, combinations thereof and the like. These forms may be assembled in any manner desired including a pipe rope wick, a wedge rope wick, a multi-rope wick and the like.

In another possible application method, liquid compositions may be selectively applied to weeds by the use of recirculating sprayer systems wherein the recirculating spray unit is mounted on a tractor or high clearance mobile equipment and the spray is directed horizontally onto the weeds growing over a crop. Spray not intercepted by the weeds is collected in a recovery chamber before contacting the crop and is reused. Roller applications may also be employed to apply liquid compositions to weeds growing over a crop.

In yet another possible application method, shielded applicators may be employed to direct the liquid composition in the form of a spray onto the weeds while effectively shielding the crops from the spray.

These and other possible application methods for selectively applying liquid compositions to weeds are discussed in detail in Innovative Methods of Post-Emergence Weed Control, McWhorter C. G, Southern Weed Science Society, 33rd Annual Meeting Proceedings, Jan. 15-17, 1980; Auburn University Printing Service, Auburn, Ala. U.S.A., the teachings of which are incorporated herein by reference in their entirety.

Another possible method of applying liquid compositions of this invention to plants includes controlled droplet application which is also known as the ultra low-volume chemical application. Controlled droplet application involves the production of uniform or nearly uniform spray drops of a predetermined size and the conveyance of these drops with negligible evaporation to a spray target. In particular, this method comprises feeding spray solutions to a rotary atomizer comprising a small disk with serrated edges that disperses liquid into droplets as the disk spins. Different droplet sizes are produced by changing solution flow rates to the spinning disk or changing the speed of rotation of the disk.

Those of skill in the art will recognize that the physical and chemical characteristics of the compound or composition employed will determine to a large extent the particular application method selected therewith.

The aforementioned and other methods for applying liquid compositions to plants are discussed in detail in "Rope Wick Applicator—Tool With A Future", Dale, James E., pp. 3–4, "The Recirculating Sprayer and Roundup® Herbicide", Derting, Claude W., pp. 5–7, and "C.D.A. Herbicide Application", McGarvey, Frank X., *Weeds Today,* Volume 11, Number 2, pp. 8–9, Late Spring, 1980, 309 W. Clark St., Champaign, Ill., the teachings of which are incorporated herein by reference in their entirety.

Although this invention has been described with respect to specific modifications, the details thereof are not to be construed as limitations, for it will be apparent that various equivalents, changes and modifications may be resorted to without departing from the spirit and scope thereof and it is understood that such equivalent embodiments are intended to be included herein.

What is claimed is:

1. A method of controlling undesired plants which comprises applying to said plants or plant growth medium a herbicidally effective amount of a compound of the formula

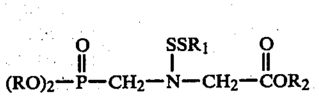

wherein R is selected from the group consisting of phenyl, naphthyl or biphenylyl; or phenyl, naphthyl or biphenylyl substituted with from 1 to 3 substituents independently selected from the group consisting of lower alkyl, lower alkoxy, lower alkylthio, alkoxycarbonyl, methylenedioxy, trifluoromethyl, cyano, nitro and halogen; $R_1$ is alkyl, cycloalkyl, aralower alkyl or phenyl or naphthyl or phenyl or naphthyl substituted with from 1 to 3 substituents independently selected from the group consisting of lower alkyl, lower alkoxy, halogen, and trifluoromethyl and nitro and $R_2$ is lower alkyl or aralower alkyl.

2. A method according to claim 1 wherein R is phenyl or phenyl substituted.

3. A method according to claim 2 wherein $R_1$ is alkyl, cycloalkyl or aralower alkyl.

4. A method according to claim 3 wherein $R_2$ is alkyl or aralower alkyl.

5. A method according to claim 4 wherein said compound is glycine, N-[(1,1-dimethylethyl)dithio]-N-[(diphenoxyphosphinyl)methyl]-, methyl ester.

6. A method according to claim 4 wherein said compound is glycine, N-[[bis(4-methoxyphenoxy)phosphinyl]methyl]-N-[[(1,1,dimethylethyl)dithio]-, ethyl ester.

7. A method according to claim 4 wherein said compound is glycine, N-[(diphenoxyphosphinyl)methyl]-N-[(1-methylethyl)dithio]-, methyl ester.

8. A method according to claim 4 wherein said compound is glycine, N-[(diphenoxyphosphinyl)methyl]-N-(octyldithio)-, methyl ester.

9. A method according to claim 4 wherein $R_2$ is methyl.

10. A method according to claim 4 wherein $R_2$ is phenylethyl.

11. A method according to claim 1 wherein $R_1$ is phenyl substituted from 1 to 3 substituents selected from the group consisting of lower alkyl, lower alkoxy, halogen, trifluoromethyl, and nitro.

12. A herbicidal composition comprising an inert adjuvant and a herbicidally effective amount of a compound of the formula

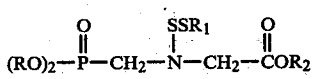

wherein R is selected from the group consisting of phenyl, naphthyl or biphenylyl; or phenyl, naphthyl or biphenylyl substituted with from 1 to 3 substituents independently selected from the group consisting of lower alkyl, lower alkoxy, lower alkylthio, alkoxycarbonyl, methylenedioxy, trifluoromethyl, cyano, nitro and halogen; $R_1$ is alkyl, cycloalkyl, aralower alkyl or phenyl or naphthyl or phenyl or naphthyl substituted with from 1 to 3 substituents independently selected from the group consisting of lower alkyl, lower alkoxy, halogen, and trifluoromethyl and nitro and $R_2$ is lower alkyl or aralower alkyl.

13. A composition according to claim 12 wherein said compound is a compound wherein R is phenyl or phenyl substituted.

14. A composition according to claim 13 wherein said compound is a compound wherein $R_1$ is alkyl, cycloalkyl or aralower alkyl.

15. A composition according to claim 14 wherein said compound is a compound wherein $R_2$ is alkyl or aralower alkyl.

16. A composition according to claim 15 wherein said compound is glycine, N-[(1,1-dimethylethyl)dithio]-N-[(diphenoxyphosphinyl)methyl]-, methyl ester.

17. A composition according to claim 15 wherein said compound is glycine, N-[[bis(4-methoxyphenoxy)phosphinyl]-methyl]-N-[[(1,1,dimethylethyl)dithio]-, ethyl ester.

18. A composition according to claim 15 wherein said compound is glycine, N-[(diphenoxyphosphinyl)methyl]-N-[(1-methylethyl)dithio]-, methyl ester.

19. A composition according to claim 15 wherein said compound is glycine, N-[(diphenoxyphosphinyl)methyl]-N-(octyldithio)-, methyl ester.

20. A composition of claim 15 wherein $R_2$ is methyl.

21. A composition of claim 15 wherein $R_2$ is phenylethyl.

22. A composition of claim 12 wherein $R_1$ is phenyl substituted with from 1 to 3 substituents selected from the group consisting of lower alkyl, lower alkoxy, halogen, trifluoromethyl, and nitro.

23. A compound of the formula

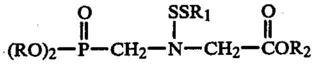

wherein R is selected from the group consisting of phenyl, naphthyl or biphenylyl; or phenyl, naphthyl or biphenylyl substituted with from 1 to 3 substituents independently selected from the group consisting of lower alkyl, lower alkoxy, lower alkylthio, alkoxycarbonyl, methylenedioxy, trifluoromethyl, cyano, nitro and halogen; $R_1$ is alkyl, cycloalkyl, aralower alkyl or phenyl or naphthyl or phenyl or naphthyl substituted with from 1 to 3 substituents independently selected from the group consisting of lower alkyl, lower alkoxy, halogen, and trifluoromethyl and nitro and $R_2$ is lower alkyl or aralower alkyl.

24. A compound according to claim 23 wherein R is phenyl or phenyl substituted.

25. A compound according to claim 24 wherein $R_1$ is alkyl, cycloalkyl or aralower alkyl.

26. A compound according to claim 25 wherein $R_2$ is lower alkyl or aralower alkyl.

27. A compound of claim 26 wherein $R_1$ is methyl.

28. A compound of claim 26 wherein $R_1$ is phenylethyl.

29. A compound of claim 24 wherein $R_1$ is phenyl substituted with from 1 to 3 substituents selected from the group consisting of lower alkyl, lower alkoxy, halogen, trifluoromethyl and nitro.

30. A compound according to claim 26 wherein the compound is glycine, N-[(1,1-dimethylethyl)dithio]-N-[(diphenoxyphosphinyl)methyl]-, methyl ester.

31. A compound according to claim 26 wherein the compound is glycine, N-[[bis(4-methoxyphenoxy)phosphinyl]methyl]-N-[[(1,1,dimethylethyl)dithio]-, ethyl ester.

32. A compound according to claim 26 wherein the compound is glycine, N-[(diphenoxyphosphinyl)methyl]-N-[(1-methylethyl)dithio]-, methyl ester.

33. A compound according to claim 26 wherein the compound is glycine, N-[(diphenoxyphosphinyl)methyl]-N-(octyldithio)-, methyl ester.

* * * * *